(12) United States Patent
Eckman et al.

(10) Patent No.: US 6,699,681 B2
(45) Date of Patent: Mar. 2, 2004

(54) ENDOTHELIN CONVERTING ENZYMES AND THE AMYLOID β PEPTIDE

(75) Inventors: Christopher B. Eckman, Ponte Vedra Beach, FL (US); Elizabeth A. Eckman, Ponte Vedra Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/824,924

(22) Filed: Apr. 3, 2001

(65) Prior Publication Data

US 2002/0091072 A1 Jul. 11, 2002

Related U.S. Application Data

(60) Provisional application No. 60/233,012, filed on Sep. 15, 2000.

(51) Int. Cl.$^7$ .............. C12Q 1/34; C12Q 1/37; C12Q 1/02; G01N 33/53; C12N 9/00
(52) U.S. Cl. .............. 435/18; 435/4; 435/23; 435/24; 435/7.1; 435/29; 435/183; 435/195; 435/212; 514/2; 530/300; 530/350
(58) Field of Search .............. 435/18, 4, 23, 435/24, 7.1, 29, 183, 195, 212, 6, 501; 514/2; 530/300, 350; 424/94.1

(56) References Cited

U.S. PATENT DOCUMENTS 5,736,376 A    4/1998   Yanagisawa

FOREIGN PATENT DOCUMENTS

WO    WO 00/65025    11/2000

OTHER PUBLICATIONS

Johnson et al., 1999, vol. 274, 7, pp. 4053–4058.*
Fuller et al., "Intracellular Production of βA4 Amyloid of Alzheimer's Disease: Modulation by Phosphoramidon and Lack of Coupling to the Secretion of the Amyloid Precursor Protein," *Biochem.*, 1995, 34(25):8091–8098.
Naidu et al., "β–Amyloid Peptide Produced in Vitro Is Degraded by Proteinases Released by Cultured Cells," *J. Biol. Chem.*, 1995, 270(3):1369–1374.
Qiu et al., "Insulin–degrading Enzyme Regulates Extracellular Levels of Amyloid β–Protein by Degradation," *J. Biol. Chem.*, 1998, 273(49):32730–32738.
Saido, "Alzheimer's Disease as Proteolytic Disorders: Anabolism and Catabolism of β–Amyloid," *Neurobiol. Of Aging*, 1998, 19(IS):S69–S75.
Takaki et al., "Biochemical Identification of the Neutral Endopeptidase Family Member Responsible for the Catabolism of Amyloid β Peptide in the Brain," *J. Biochem.*, 2000, 128:897–902.
Tummolo et al., "Quantification of Alzheimer's β–amyloid peptide levels in the plasma, CSF and brain tissue from guinea pig following administration of classical proteases inhibitors," *Soc. Neurosci.*, 1996, 22(2):1170, Abstract #461.10.
Brown et al., "Functional Significance of the Isoforms of Endothelin–Converting Enzyme–1," *J. Cardiovasc. Pharmacol.*, 2000, 36(Suppl. 1):S26–S27.
Eckman et al., "Degradation of the Alzheimer's Amyloid β Peptide by Endothelin–converting Enzyme," *J. Biol. Chem.*, 2001, 276(27):24540–24548.

* cited by examiner

*Primary Examiner*—John Ulm
*Assistant Examiner*—Olga N. Chernyshev
(74) *Attorney, Agent, or Firm*—Fish & Richardson P.C., P.A.

(57) ABSTRACT

The invention describes catabolism of Aβ by endothelin converting enzymes (ECEs). Methods of identifying compounds that upregulate ECEs are provided by the invention. Further provided by the invention are methods of regulating Aβ catabolism in a cell and methods of decreasing the amount of Aβ in a cell. The invention discloses methods of diagnosing an individual with AD and methods of treating such an individual. The invention further discloses methods of identifying compounds that have anti-hypertension activity but do not cause an increase in the level of Aβ. Further, the invention provides mutant ECE nucleic acids and mutant ECE polypeptides.

16 Claims, No Drawings

SEQUENCE LISTING

```
<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<223> OTHER INFORMATION: Primer for PCR

<400> SEQUENCE: 1
```

-continued caggaattcg ccaccatgcc tctccagggc ctgggcctgc                              40

<210> SEQ ID NO 2
<211> LENGTH: 36
<212> TYPE: DNA
<213> ORGANISM: Artificial Sequence
<220> FEATURE:
<223> OTHER INFORMATION: Primer for PCR

<400> SEQUENCE: 2
caggaattcg ccaccatgcg gggcgtgtgg ccgccc                                  36

<210> SEQ ID NO 3
<211> LENGTH: 22
<212> TYPE: DNA
<213> ORGANISM: Artificial Sequence
<220> FEATURE:
<223> OTHER INFORMATION: Primer for PCR

<400> SEQUENCE: 3
cagcagcttc cccagctgga cc                                                 22

<210> SEQ ID NO 4
<211> LENGTH: 22
<212> TYPE: DNA
<213> ORGANISM: Artificial Sequence
<220> FEATURE:
<223> OTHER INFORMATION: Primer for PCR

<400> SEQUENCE: 4
ggtccagctg gggaagctgc tg                                                 22

<210> SEQ ID NO 5
<211> LENGTH: 36
<212> TYPE: DNA
<213> ORGANISM: Artificial Sequence
<220> FEATURE:
<223> OTHER INFORMATION: Primer for PCR

<400> SEQUENCE: 5
gctctagatt accagacttc gcacttgtga ggcggg                                  36

<210> SEQ ID NO 6
<211> LENGTH: 31
<212> TYPE: DNA
<213> ORGANISM: Artificial Sequence
<220> FEATURE:
<223> OTHER INFORMATION: Primer for PCR

<400> SEQUENCE: 6
gagagaattc tcagtaccag acaagatccc c                                       31

<210> SEQ ID NO 7
<211> LENGTH: 41
<212> TYPE: DNA
<213> ORGANISM: Artificial Sequence
<220> FEATURE:
<223> OTHER INFORMATION: Primer for PCR

<400> SEQUENCE: 7
cgttttcctt ttgcggccgc ccagacttcg cacttgtgag g                            41

<210> SEQ ID NO 8
<211> LENGTH: 10
<212> TYPE: PRT
<213> ORGANISM: Artificial Sequence -continued

```
<220> FEATURE:
<223> OTHER INFORMATION: Consensus sequence for endothelin converting
      enzymes
<220> FEATURE:
<221> NAME/KEY: VARIANT
<222> LOCATION: 1
<223> OTHER INFORMATION: Gly, Ser, Thr, Ala, Leu, Ile, Val or Asn
<220> FEATURE:
<221> NAME/KEY: VARIANT
<222> LOCATION: 2, 3, 9
<223> OTHER INFORMATION: Any amino acid
<220> FEATURE:
<221> NAME/KEY: VARIANT
<222> LOCATION: 6
<223> OTHER INFORMATION: Leu, Ile, Val, Met, Phe, Tyr or Trp
<220> FEATURE:
<221> NAME/KEY: VARIANT
<222> LOCATION: 7
<223> OTHER INFORMATION: Any amino acid except Asp, Glu, His, Arg,
      Lys or Pro
<220> FEATURE:
<221> NAME/KEY: VARIANT
<222> LOCATION: 10
<223> OTHER INFORMATION: Leu, Ile, Val, Met, Phe, Tyr, Trp, Gly, Ser,
      Pro or Gln

<400> SEQUENCE: 8

Xaa Xaa Xaa His Glu Xaa Xaa His Xaa Xaa
 1               5                  10
```

US 6,699,681 B2

ENDOTHELIN CONVERTING ENZYMES AND THE AMYLOID β PEPTIDE

CROSS REFERENCE TO RELATED APPLICATIONS

This application claims benefit of priority under 35 U.S.C. §119(e) to U.S. provisional application serial No. 60/233,012, filed Sep. 15, 2000.

TECHNICAL FIELD

This invention relates to Alzheimer's disease, and more particularly, to catabolism of Aβ.

BACKGROUND

Alzheimer's disease (AD) is the most common cause of dementia in the elderly and is characterized pathologically by the accumulation of β-amyloid polypeptides (Aβ) in the brain in the form of senile plaques. Aβ is produced from the amyloid precursor protein (APP) through the combined proteolytic actions of β and γ secretase and is then secreted into the extracellular milieu.

SUMMARY

The invention identifies endothelin-converting enzymes (ECE) as Aβ degrading enzymes. The invention features methods of identifying compounds that increase expression or activity of an ECE. Methods are also provided to increase the catabolism of Aβ in a cell, for example by decreasing or abolishing the activity of an ECE inhibitor or, alternatively, by reducing degradation of ECE. In addition, methods of treating an individual with AD are provided. As ECE inhibitors are currently being evaluated for anti-hypertension activity, the invention also features methods of identifying anti-hypertension compounds that do not cause an increase in the level of Aβ. Mutants of ECE polypeptides are also provided by the invention, as are mutant ECE nucleic acids. Such mutant ECE nucleic acids and polypeptides can be used to diagnose an individual with AD or those having a predisposition for AD.

In one aspect, the invention provides methods of identifying a compound that increases expression of an ECE nucleic acid, including contacting cells comprising an ECE nucleic acid with a compound and detecting the amount of ECE RNA or ECE polypeptide. An increase in the amount of ECE RNA or polypeptide in the presence of the compound compared to the amount produced in the absence of the compound indicates that the compound increases expression of an ECE nucleic acid. ECE RNA and ECE polypeptides are typically detected using Northern blots and Western blots, respectively. Representative examples of cells include H4 neuroglioma cells, CHO cells and HUVEC cells. Alternatively, the effect of a compound on the expression of an ECE nucleic acid also can be determined using a cell-free transcription/translation system.

The invention further provides methods of identifying compounds that increase activity of an ECE polypeptide, including contacting Aβ with an ECE polypeptide in the presence of the compound and detecting the amount of unhydrolyzed Aβ. Generally, a decrease in the amount of unhydrolyzed Aβ produced in the presence of the compound compared to the amount produced in the absence of the compound is an indication that the compound increases activity of an ECE polypeptide. In one embodiment, the ECE nucleic acid or polypeptide and the Aβ are together in a cell. Generally, the unhydrolyzed Aβ is detected using one of many immunoassays available in the art.

In another aspect, the invention provides methods of identifying a compound that increases catabolism of Aβ, including performing a big-ET conversion assay in the presence or absence of the compound. Typically, an increase in the amount of mature ET in the presence of the compound compared to the amount in the absence of the compound indicates a compound that increases catabolism of Aβ.

In yet another aspect, the invention provides methods of identifying a compound that has anti-hypertension activity but does not cause an increase in the level of Aβ. The methods include contacting Aβ with an ECE nucleic acid or polypeptide in the presence of the compound, detecting the amount of unhydrolyzed Aβ, and determining the anti-hypertension activity of the compound. Generally, a lack of an increase in the amount of unhydrolyzed Aβ produced in the presence of the compound compared to the amount produced in the absence of the compound is an indication that the compound does not cause an increase in ECE activity. If necessary, the anti-hypertension activity of a compound can be determined using an animal model, such as a spontaneously hypersensitive rat (SHR).

In still another aspect of the invention, there are provided methods of determining that an anti-hypertension compound or candidate compound does not cause an increase in the level of Aβ, including contacting Aβ with an ECE nucleic acid or polypeptide in the presence of the anti-hypertension compound or candidate compound and detecting the amount of unhydrolyzed Aβ. A lack of an increase in the amount of unhydrolyzed Aβ produced in the presence of the compound compared to the amount produced in the absence of the compound is an indication that the compound does not cause an increase in ECE activity. The anti-hypertension compound or candidate compound can be, for example, an ECE inhibitor.

In an aspect of the invention, there are provided methods of increasing intracellular or extracellular Aβ catabolism, including administering a compound to a cell. A compound can decrease or abolish the activity of an inhibitor of an ECE polypeptide or can decrease the degradation of an ECE polypeptide.

In another aspect of the invention, there are provided methods of decreasing the amount of Aβ in a cell by administering a vector. In one embodiment, a vector includes an ECE nucleic acid and elements necessary for expression operably linked to the ECE nucleic acid. The ECE nucleic acid can be introduced to cells in vitro or in vivo.

In another aspect of the invention, there are provided methods of treating an individual having AD, including administering a vector to the individual. The vector typically includes an ECE nucleic acid and elements necessary for expression operably linked to the ECE nucleic acid. In one embodiment, the vector is targeted to the brain of the individual.

In yet another aspect of the invention, there are provided methods of treating an individual having AD, including administering an ECE polypeptide to the individual. An ECE polypeptide can be administered directly into the brain of the individual.

The invention further provides ECE-selective inhibitors. It is preferred that cells or the blood-brain barrier be impermeable to such ECE-selective inhibitors.

It is another aspect of the invention to provide isolated mutant ECE polypeptides. In one embodiment, mutant ECE polypeptides exhibit altered Aβ hydrolysis properties compared to a corresponding wild-type ECE polypeptide. Such altered Aβ hydrolysis properties can result in decreased catabolism of Aβ or an accumulation of Aβ, and/or result in or contribute to AD. Altered Aβ hydrolysis properties also can be associated with an increased risk for AD in an individual. Also provided by the invention are isolated mutant ECE nucleic acids. Mutant ECE nucleic acids can include promoter and/or regulatory sequences and additionally or alternatively can include coding sequences.

In yet another aspect, the invention provides methods of diagnosing an individual having AD or having an altered predisposition for AD. The methods include detecting the presence or absence of one or more mutant ECE nucleic acid molecules in a biological sample from the individual. The presence of the mutant ECE nucleic acid is indicative of an individual having AD or having an altered predisposition (e.g., an increased predisposition) for AD. Representative biological samples include blood, serum, cerebrospinal fluid, brain and skin.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

Deposition of Aβ polypeptides in the brain is an early and invariant feature of AD. As with any protein, the concentration of Aβ is determined not only by its production, but also by its catabolism. Significantly, it is predicted that a reduction in Aβ catabolism of 30–50% can be equivalent to a 50–100% increase in production (Saido et al., 1998, *Neurobiol. Aging*, 19(Suppl.):69–75).

The invention identifies ECEs as Aβ degrading enzymes. Prior to this invention, ECEs were named and recognized primarily for their ability to hydrolyze big endothelin precursor peptides (e.g., big ET-1) to produce the endothelin family of potent vasoconstrictors (e.g., ET-1).

Aβ Catabolism by ECE

It is a feature of the invention to provide methods of identifying compounds that increase expression of ECE nucleic acids or that increase activity of ECE polypeptides. Up-regulation of ECE to increase either or both intracellular and extracellular catabolism of Aβ can be therapeutically useful for the treatment of AD. A compound is identified as up-regulating an ECE nucleic acid if the amount of ECE RNA or ECE polypeptide increases in the presence of the compound and an ECE nucleic acid. The amount of ECE RNA or ECE polypeptides can be determined using methods known in the art (e.g., Northern blotting or Western blotting, respectively). See Sambrook, Fritsch & Maniatis, *Molecular Cloning: A Laboratory Manual*, 2nd Ed., 1989, Cold Spring Harbor Laboratory Press. A compound is identified as up-regulating activity of an ECE polypeptide if the amount of unhydrolyzed Aβ decreases in the presence of the compound and an ECE. Alternatively, an increase in hydrolyzed Aβ products can be used to identify compounds that increase activity of ECE polypeptides.

As used herein, a "compound" refers to, without limitation, a biological macromolecule, such as an oligonucleotide or a polypeptide, a chemical compound, a mixture of chemical compounds, or an extract or fraction isolated from bacterial, plant, fungal or animal matter. As used herein, an Aβ polypeptide refers to a portion of an APP (e.g., human APP) that is produced following cleavage by β-secretase and γ-secretase (for example, residues 671–711 (Aβ40) or 671–713 (Aβ42) of GenBank Accession No. D87675). An Aβ polypeptide can have from 39 to 43 amino acid residues (e.g., 39, 40, 41, 42 or 43 residues). As used herein, "unhydrolyzed Aβ" refers to a full-length Aβ polypeptide that has not been cleaved, hydrolyzed, degraded or catabolized, i.e., Aβ polypeptides that are from 39 to 43 residues in length.

Alternatively, a big ET conversion assay can be performed in the presence or absence of a compound. Compounds that increase the conversion of big-ET precursors to mature ETs also can increase catabolism of Aβ. Such compounds can be therapeutically useful for the treatment of AD. Methods have been described for detecting conversion of big ET-1 to mature ET-1 as an assay for ECE activity (McMahon et al., 1991, *J. Cardiovasc. Pharmacol.*, 17 (Suppl. 7):S29–S33; Auguet et al., 1992, *Eur. J. Pharmacol.*, 224:101–102; and Xu et al., 1994, *Cell*, 78:473–485).

Methods of increasing catabolism of Aβ represent another feature of the invention, and include administering a compound to a cell such that expression of an ECE nucleic acid or activity of an ECE polypeptide is increased. Without being bound by a particular mechanism, compounds that up-regulate ECE can act directly on an ECE nucleic acid or on the ECE polypeptide itself (e.g., by increasing transcription and/or translation of ECE nucleic acids, or increasing the catalytic activity of an ECE polypeptide) or indirectly (e.g., by decreasing or abolishing the activity of a repressor of an ECE nucleic acid or an inhibitor of an ECE polypeptide, or by decreasing degradation of an ECE polypeptide).

ECE Nucleic Acids and Polypeptides

ECEs (3.4.24.71) are a class of structurally- and functionally-related type II integral membrane zinc metalloproteases named for their ability to hydrolyze a family of biologically inactive intermediates, big ETs, exclusively at a Trp/Val-Ile bond at amino acid residues 21–22 to form the potent vasoconstrictors, ET. Human ECE-1 exists as four isoforms that are produced using alternate promoters at a single locus on chromosome 1 (1p36) (Valdenaire et al., 1999, *Eur. J. Biochem.*, 264:341–349 and references therein). The four isoforms each hydrolyze big ETs with equal efficiency, but differ in their subcellular localization and tissue distribution (see, for example, Schweizer et al., 1997, *Biochem. J.*, 328:871–7; Azarani et al., 1998, *Biochem. J.*, 333:439–448; Cailler et al., 1999, *Biochem. J.*, 341:119–126; Valdenaire et al., 1999, *J. Cell Sci.*, 112:3115–25; Valdenaire et al., 1999, *Eur. J. Biochem.*, 264:341–9; Emoto et al., 1999, *J. Biol. Chem.*, 274:1509–18). Human ECE-2 is encoded by a separate gene and has about 60% overall identity to ECE-1. ECE-2 is localized to an intracellular compartment, and has an acidic pH optimum (Emoto & Yanagisawa, 1995, *J. Biol. Chem.*, 270:15262–15268). Both ECE-1 and ECE-2 preferentially hydrolyze big ET-1 and both are highly glycosylated. ECE-2 is most abundantly expressed in neural tissues. ECE-3 has also been purified and is highly specific for the conversion of big ET-3.

The invention features isolated ECE polypeptides. "ECE polypeptide" refers to a polypeptide having at least functional ECE activity (e.g., possessing the ability to specifically hydrolyze big ETs to produce mature ETs, or to hydrolyze Aβ). ECE polypeptides can include, but do not necessarily require, the entire ECE coding region. ECE polypeptides include known ECE polypeptides (e.g., ECE-1a, ECE-1b, ECE-1c, ECE-1d, ECE-2, and ECE-3). Representative examples of sequences corresponding to known ECE polypeptides include, but are not limited to: GenBank Accession Nos. P42892, XP 001827, JC4136, JC2521, AAG28399, NP 001388, O60344, CAB52285, BAA83687, CAB46443, AAD21221, AAD08993, CAA66922, BAA07800, BAA08442, CAA63016, CAA63015 and CAA84548 disclosing amino acid sequences of ECE polypeptides from human (*Homo sapiens*); GenBank Accession Nos. S47268, A54667, Q10711, P42891, S51010, CAA84547, AAA82927 and AAA82928 disclosing amino acid sequences of ECE polypeptides from cattle (*Bos taurus*); GenBank Accession Nos. A53679, P42893, BAA06152, CAB46529, CAB46528 and BAA09864 disclosing amino acid sequences of ECE polypeptides from rat (*Rattus norvegicus*); GenBank Accession No. AAG09052 disclosing an amino acid sequence of an ECE polypeptide from sheep (*Ovis aries*); GenBank Accession No. AAF98287 disclosing an amino acid sequence of an ECE polypeptide from chicken (*Gallus gallus*); GenBank Accession No. AAD46624 disclosing an amino acid sequence of an ECE polypeptide from hydra (*Hydra vulgaris*); and GenBank Accession No. BAA13967 disclosing an amino acid sequence of an ECE polypeptide from pig (*Sus scrofa*). Additional sequences of ECE polypeptides can be obtained from GenBank using, for example, a search query such as "endothelin converting enzyme". Fragments, including functional fragments (i.e., having functional ECE activity as defined herein) of any of the above ECE polypeptides also are provided by the present invention.

The invention further provides isolated ECE nucleic acids. ECE nucleic acids can refer to nucleic acid sequences that encode a functional ECE polypeptide as defined above. ECE nucleic acid sequences can include those that encode only the residues required for functional ECE activity or can include sequences corresponding to the entire coding sequence. ECE nucleic acid sequences can additionally or alternatively include regulatory elements affecting expression of such coding sequences. ECE nucleic acid sequences from numerous organisms are known (e.g., human, Xenopus, mouse, rat, chicken, cow, pig, *C. elegans*, Arabidopsis, *Mycobacterium leprae, Schistosoma japonicum*). ECE nucleic acid sequences also can be obtained by known methods (e.g., searching a database, or cross-referencing from the above-identified ECE polypeptides). Representative nucleic acid sequences encoding human ECE polypeptides include GenBank Accession Nos. NM 001397 and Z35307. Alternatively, an ECE polypeptide (e.g., GenBank Accession No. JC2521) can be used to design an ECE nucleic acid.

As used herein, "isolated ECE polypeptide" refers to an ECE polypeptide that has been removed from its natural environment, i.e., it has been separated from cellular components that naturally accompany it. Typically, an ECE polypeptide is isolated when it is at least 60% (e.g., 70%, 80%, 90%, 95%, or 99%), by weight, free from proteins and molecules that are naturally associated with it.

As used herein, "isolated nucleic acid" refers to a nucleic acid corresponding to part or all of a gene encoding an ECE polypeptide, but free of sequences that normally flank one or both sides of the wild-type gene in a naturally occurring genome. The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a cDNA or genomic DNA fragment produced by PCR or restriction endonuclease digestion) independent of other sequences, as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid molecule. A nucleic acid existing among hundreds to millions of other nucleic acids within, for example, cDNA libraries or genomic libraries, or gel slices containing a genomic DNA restriction digest, is not to be considered an isolated nucleic acid.

Isolated ECE nucleic acid molecules of the invention are at least about 20 nucleotides in length. For example, the nucleic acid molecule can be about 20, 30, 40, 50, 75, 100, or greater than 100 nucleotides in length, e.g., 150, 200, 300, 400, 500, or 1000 nucleotides in length. Such fragments, whether protein-encoding or not, can be used as probes, primers, and diagnostic reagents. In some embodiments, the isolated nucleic acid molecules encode a full-length ECE polypeptide. Nucleic acid molecules can be DNA or RNA, linear or circular, and in sense or antisense orientation.

Isolated nucleic acid molecules of the invention can be produced by standard techniques. Isolated nucleic acids within the scope of the invention can be obtained using any method including, without limitation, common molecular cloning and chemical nucleic acid synthesis techniques. For example, polymerase chain reaction (PCR) techniques can be used to obtain an isolated nucleic acid having a sequence that shares identity with art known ECE sequences. PCR refers to a procedure or technique in which target nucleic acids are amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. When using RNA as a source of template, reverse transcriptase can be used to synthesize complimentary DNA (cDNA) strands. Primers are typically 14 to 40 nucleotides in length, but can range from 10 nucleotides to hundreds of nucleotides in length. General PCR techniques are described, for example in *PCR Primer: A Laboratory Manual*, Dieffenbach & Dveksler, Eds., Cold Spring Harbor Laboratory Press, 1995.

Isolated nucleic acids of the invention also can be chemically synthesized, either as a single nucleic acid molecule or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a double-stranded nucleic acid molecule per oligonucleotide pair, which then can be ligated into a vector.

In addition, nucleic acid and amino acid databases (e.g., GenBank) can be used to obtain an isolated polynucleotide within the scope of the invention. For example, a sequence having homology to a nucleic acid sequence encoding an art known ECE polypeptide or an amino acid sequence having homology to an art known ECE amino acid sequence can be used as a query to search a database (e.g., GenBank).

Furthermore, nucleic acid hybridization techniques can be used to obtain an isolated nucleic acid within the scope of the invention. Briefly, a nucleic acid sequence encoding an ECE polypeptide can be used as a probe to identify a similar nucleic acid by hybridization under conditions of moderate to high stringency. Moderately stringent hybridization conditions include hybridization at about 42° C. in a hybridization solution containing 25 mM $KPO_4$ (pH 7.4), 5×SSC, 5×Denhart's solution, 50 µg/ml denatured, sonicated salmon sperm DNA, 50% formamide, 10% Dextran sulfate, and 1–15 ng/ml probe (about $5 \times 10^7$ cpm/µg), and wash steps at about 50° C. with a wash solution containing 2×SSC and 0.1% SDS. For high stringency, the same hybridization conditions can be used, but washes are performed at about 65° C. with a wash solution containing 0.2×SSC and 0.1% SDS.

Once a nucleic acid is identified, the nucleic acid then can be purified, sequenced, and analyzed to determine whether it is within the scope of the invention as described herein. Hybridization can be done by Southern or Northern analysis to identify DNA or RNA sequences, respectively, that hybridize to a probe. The probe can be labeled with biotin, digoxygenin, an enzyme, or a radioisotope such as $^{32}$P or $^{35}$S. The DNA or RNA to be analyzed can be electrophoretically separated on an agarose or polyacrylamide gel, transferred to nitrocellulose, nylon, or other suitable membrane, and hybridized with the probe using standard techniques well known in the art. See, for example, sections 7.39–7.52 of Sambrook, Fritsch & Maniatis, *Molecular Cloning: A Laboratory Manual*, 2nd Ed., 1989, Cold Spring Harbor Laboratory Press, Plainview, N.Y.

The invention also features isolated mutant ECE polypeptides that exhibit altered or abolished Aβ hydrolysis properties compared to corresponding wild-type ECE nucleic acids or polypeptides. Mutant ECE polypeptides can be identified that are causative of Alzheimer's disease or that contribute to an increased risk of AD in certain individuals. Unless otherwise specified, mutant ECE polypeptides refer to ECE polypeptides that have lost either or both endothelin converting activity or Aβ hydrolysis activity. In addition, mutant ECE polypeptides refer to functional ECE polypeptides that have altered enzyme activity (e.g., increased or decreased $K_m$ or $V_{max}$) compared to corresponding wild-type ECE polypeptides.

The invention also features isolated mutant ECE nucleic acids. Mutant ECE nucleic acids refer to mutations in ECE nucleic acid sequences (e.g., coding, or regulatory) that encode mutant ECE polypeptides, or that encode functional ECE polypeptides that are inappropriately expressed (e.g., temporally, spatially, or developmentally) or inappropriately catabolized when compared with corresponding wild-type ECE polypeptides.

Types of mutations that an ECE nucleic acid can carry include, without limitation, insertions, deletions, transitions, transversions and inversions. An ECE nucleic acid can include more than one mutation and more than one type of mutation. Such mutations, if present within the coding sequence, can result in insertions or deletions of one or more amino acids into an ECE polypeptide, conservative or non-conservative amino acid substitutions within an ECE polypeptide or premature termination of an ECE polypeptide. Insertion or deletion of amino acids can, for example, disrupt the conformation of essential α-helical or β-pleated sheet regions, and can also disrupt binding or catalytic sites important for enzymatic activity. Non-conservative amino acid substitutions can result in a substantial change in the bulk of the residue side chain, and ultimately can make a substantial change in the charge, hydrophobicity, or structure of a polypeptide. Premature termination also can cause disruptions in secondary and tertiary polypeptide structure. In addition, non-coding sequence mutations (i.e., mutations in a promoter, regulatory element, or untranslated region) can alter the expression pattern properties (e.g., temporal, spatial, or developmental) of an ECE polypeptide, by, for example, changing the binding characteristics of a cis-acting transcription factor.

The effect of mutations in ECE nucleic acids and ECE polypeptides can be examined through various approaches including, but not limited to, comparing individuals that have a mutation within an ECE nucleic acid to individuals lacking such a mutation, or expressing (e.g., overexpressing) a mutant ECE nucleic acid in a cell. The effect of mutations in an ECE nucleic acid and the encoded polypeptide can be evaluated by measuring the amount of mature ET or the amount of Aβ (e.g., unhydrolyzed Aβ).

Site-directed mutagenesis previously has been performed on ECEs, as well as on related zinc metalloendopeptidases (e.g., neprilysin (NEP), thermolysin) to identify important residues (see Shimada et al., 1996, *Biochem J.*, 315:863–7; Hoang et al., 1997, *Biochem J.*, 327:925–9; Savage et at, 1998, *J. Cardiovasc. Pharmacol.*, 31(Suppl.):S16–18; Marie-Claire et al., 1999, *J. Mol. Biol.*, 285:1911–5). A typical ECE-1, for example, has a short N-terminal tail (about 50 residues), one or more hydrophobic transmembrane domains (usually about 20 residues) and a large domain that includes a zinc-binding motif common to catalytic domains of metalloproteases (about 680 residues). The residues acting as zinc ligands and those involved in the catalytic activity are known, and include two histidines (H) that bind zinc and are very close together in the sequence, and an active site glutamic acid (E) residue C-terminal to the first histidine that acts as a nucleophile and promotes the attack on the carbonyl carbon of the substrate by a water molecule. The consensus pattern for ECE enzymes is as follows: [GSTALIVN]-x(2)-H-E-[LIVMFYW]-{DEHRKP}-H-x-[LIVMFYWGSPQ] (SEQ ID NO: 8) (ProSite Accession No. PS00142 and ProSite Documentation PDOC00129; for information regarding ProSite prefixes, refer to Sonhammer et al. (1997) *Protein* 28:405–420). ECE-1 also has a number of cysteine residues that are conserved among, at least one of which is involved in disulphide-linked homodimerization and other(s) that can be palmitoylated.

A representative human ECE-1 amino acid sequence (i.e., NM 001397) is predicted to have the following: ten putative N-glycosylation sites (PS00001); one putative glycosaminoglycan attachment site (PS00002); three putative cAMP- and cGMP-dependent protein kinase phosyphorylation sites (PS00004); ten putative protein kinase C phosphorylation sites (PS00005); sixteen to eighteen putative casein kinase II phosphorylation sites (PS00006); three putative tyrosine kinase phosphorylation sites (PS00007); nine to ten putative N-myristoylation sites (PS00008); and one putative neutral zinc metallopeptidase zinc-binding region signature domain (PS00142). In addition, glycosylation can be important for full enzymatic activity of ECE-1. The above examples are representative only, and those of skill are aware that any position along an ECE nucleic acid sequence represents a site of potential mutation.

Vectors containing a wild type or mutant ECE nucleic acid also are provided by the invention. Vectors, including expression vectors, suitable for use in the present invention are commercially available and/or produced by recombinant DNA technology methods routine in the art. A vector containing an ECE nucleic acid sequence additionally can have elements necessary for expression operably linked to such an ECE nucleic acid, and further can include sequences such as those encoding a selectable marker (e.g., an antibiotic resistance gene), and/or those that can be used in purification of an ECE polypeptide (e.g., 6×His tag). Elements necessary for expression include nucleic acid sequences that direct and regulate expression of ECE coding sequences. One example of an element necessary for expression is a promoter sequence, for example, an ECE promoter (e.g., GenBank Accession No. AJ011770) or a non-ECE promoter. Elements necessary for expression also can include introns, enhancer sequences, response elements, or inducible elements that modulate expression of an ECE nucleic acid. Elements necessary for expression can be of bacterial, yeast, insect, mammalian, or viral origin and vectors can contain a combination of elements from different origins. As used herein, operably linked means that a promoter and/or other regulatory element(s) are positioned in a vector relative to an ECE nucleic acid in such a way as to direct or regulate expression of the ECE nucleic acid. Many methods for introducing nucleic acids into cells, both in vivo and in vitro, are well known to those skilled in the art and include, without limitation, calcium phosphate precipitation, electroporation, heat shock, lipofection, microinjection, and viral-mediated nucleic acid transfer.

Methods of Detecting Aβ

Methods for detecting unhydrolyzed Aβ in cell culture (e.g., secreted into the media) or in biological samples are known to those of skill in the art. One method is described in the Examples below, and includes using a highly specific sandwich ELISA and a BAN-50 antibody, which specifically captures Aβ polypeptides at the N-terminus, and then either a BA-27 antibody, which detects only full-length Aβ polypeptides ending at position 40, or a BC-05 antibody, which detects only full-length Aβ polypeptides ending at position 42 (Suzuki et al., 1994, *Science*, 264:1336–40; Asami-Odaka et al., 1995, *Biochem.*, 34:10272–8).

Suitable antibodies that detect an antigen within Aβ (or within the Aβ portion of APP) are also commercially available from a variety of sources, including, but not limited to, Biosource International (Camarillo, Calif.), Senetek PLC (London, England), Zymed Laboratories (San Francisco, Calif.), Peninsula Laboratories (San Carlos, Calif.) and Boehringer Mannheim (Indianapolis, Ind.). In addition, BNT-77 is an antibody that captures rodent Aβ, (Asami-Odaka et al., 1995, *Biochem.*, 34:10272–8) and can be used in conjunction with the BA-27 or BC-05 antibodies described above.

In addition to the sandwich ELISA described herein, immunoassay formats such as Western blots or immunoprecipitations may be used to detect Aβ and are well known in the art. See, *Short Protocols in Molecular Biology*, Ch. 11, John Wiley & Sons, Ed., Ausubel et al., 1992. Solid-phase immunoassays include competition immunoassays, immobilized-antigen immunoassays, immobilized-antibody immunoassays, and double-antibody immunoassays.

Western blotting typically includes the steps of electrophoretically separating ligands (e.g., proteins); transferring the ligands from the separation medium (e.g., a gel) to a solid support (e.g., nitrocellulose, nylon); and probing with antibodies that react specifically with antigenic epitopes displayed by the target protein attached to the solid support. Probing can be direct (e.g., a labeled primary antibody) or indirect (e.g., an unlabeled antibody specific for the target protein, which is subsequently detected with a labeled secondary immunological reagent, for example, protein A or anti-immunoglobulin).

Immunoprecipitation methods generally include the following steps: radiolabeling cells expressing the target protein; lysing the cells; forming specific immune complexes; collecting and purifying the immune complexes; and analyzing the radiolabeled proteins in the immunoprecipitate. Immunoprecipitation is often used to detect and quantitate target antigens in complex mixtures of proteins. Immunoprecipitation can be used to analyze proteins from unlabeled cells, provided sufficiently sensitive methods are available to detect the target protein after it has been dissociated from the antibody.

A detectable label, e.g., a radioactive label (e.g., $^3$H, $^{125}$I, $^{131}$I, $^{32}$P, $^{35}$S, and $^{14}$C) or a non-radioactive label (e.g., a fluorescent label, a chemiluminescent label, a paramagnetic label, or an enzyme label) may be attached to an antibody or fragment thereof using techniques known to those of ordinary skill in the art. Examples of enzyme labels used routinely in the art for detection and quantitation include horseradish peroxidase (HRP) and alkaline phosphatase (AP). The substrates available for either HRP or AP labels are known in the art and can be selected based upon the desired method of detecting complex formation (e.g., a fluorogenic, chemiluminescent or calorimetric signal).

Aβ that has been detected by any of the methods described herein or other methods known to those of skill in the art can be visualized or quantitated using methods routine in the art, including autoradiography of a radioactive label (e.g., x-ray film, phosphorimaging, or densitometric analysis) and spectrophotometry of a fluorescent label or of a colorimetric reaction produced by, for example, an enzymatic label. In addition, a non-Aβ polypeptide also can be detected and quantitated (e.g., for normalization purposes).

In addition, mass spectrometry (MS) can be used to detect and quantitate Aβ polypeptides. Several types of MS are available and routinely used in the art, and include Fourier-transform MS, Ion-trap MS, Magnetic-sector MS, Quadropole MS and Time-of-flight (TOF) MS. By way of example, Ciphergen (Fremont, Calif.) sells a biochip system for capturing Aβ polypeptides from culture medium or a biological sample and utilizes SELDI technology (Surface-Enhanced Laser Desorption/Ionization) with TOF-MS to detect and quantitate the level of an Aβ polypeptide.

Neuritic plaques in the brain of an individual with AD can be detected and/or monitored in vivo using an Aβ polypeptide covalently modified with a polyamine (e.g., putrescine, spermidine, or spermine) (Wengenack et al., 2000, *Nat Biotechnol.*, 18:868–72). A radiolabeled polyamine-modified Aβ polypeptide can be administered to an individual intravenously and detected using standard methods. For example, a radiolabel suitable for diagnostic imaging can be used (e.g., $^{123}$I) and detected using single photon emission computed tomography (SPECT).

ECE and Alzheimer's Disease

The invention also features methods for diagnosing an individual with AD or an individual that is predisposed to develop AD. Instances of AD may be attributable to mutations in one or more ECEs, resulting in decreased or abolished Aβ catabolism. Therefore, the methods of diagnosis described herein are based upon detection of one or more mutations in an ECE nucleic acid or an ECE polypeptide. Significantly, sib-pair analyses of genetic factors contributing to late onset AD have not excluded the region on chromosome 1 where the ECE-1 gene is located. In addition, endothelin levels have been reported to be decreased in the CSF of individuals diagnosed with AD compared to non-demented individuals. Also important is the identification of individuals with normally high levels of ECE polypeptide(s) or ECE polypeptide activity that are at a reduced risk for AD.

The identification of enzymes such as ECE that catabolize Aβ makes possible novel therapeutics aimed at reducing Aβ concentration by enhancing its removal. Accordingly, the invention features methods of treating an individual having AD by increasing the level of ECE polypeptides available to catabolize Aβ. The level of ECE polypeptides can be increased in vivo by administering a vector appropriately expressing an ECE nucleic acid to the individual.

Vectors for administering nucleic acids that encode biologically useful proteins (e.g., an ECE polypeptide) to an individual are known in the art. Current virus-based nucleic acid delivery vectors are typically derived from animal viruses, such as adenovirus, adeno-associated virus, retroviruses, lentiviruses, vaccinia virus, herpes viruses and bovine papilloma virus. Vectors for nucleic acid delivery usually have been genetically modified such that the native tropism and pathogenicity of the virus have been altered or removed. The genome of a virus also can be modified to increase its infectivity and to accommodate packaging of nucleic acids encoding, for example, a biologically useful protein. In addition, non-viral vectors and methods of using such vectors for nucleic acid delivery are known to those of skill in the art. The following descriptions are representative examples only.

Retroviruses typically mediate high nucleic acid transfer efficiency and expression. Retroviruses have an RNA genome that replicates through a DNA intermediate. Retroviruses enter a cell by direct fusion to the plasma membrane and integrate into the host chromosome during cell division. Lentiviruses are a genus of retroviruses that includes human immunodeficiency virus (HIV). Lentiviruses, unlike other retroviruses, are able to infect non-dividing cells and have been shown to infect and express nucleic acid in neuronal cells.

Adenoviruses contain a linear double-stranded DNA genome that can be engineered to inactivate its ability to replicate in the normal lytic life cycle. Adenoviruses enter a cell by receptor-mediated endocytosis and do not integrate into the genome of a host organism. Adenoviruses, therefore, are able to infect dividing or non-dividing cells. The native tropism of adenovirus is for a receptor naturally found on epithelial cells. Adenoviral vectors have been introduced and efficiently expressed in the cerebrospinal fluid of dogs and in the brain of rats, indicating successful adenoviral-mediated gene transfer to cerebral circulation.

Adeno-associated viruses have a single-stranded DNA genome, and demonstrate a broad range of tropism and infectivity, although they exhibit no human pathogenicity. Adeno-associated viruses exhibit site-specific integration and can infect non-dividing cells. Muscle cells and neurons have been the most efficient targets for nucleic acid delivery by adeno-associated viruses, and receptors and co-receptors for adeno-associated viruses have been identified.

The ability of herpes simplex virus type 1 (HSV-1) to establish a lifelong latent infection within neurons has led to interest in the use of herpes viruses as neuronal gene delivery vectors. HSV-1 contains a DNA genome and can package large amounts of foreign DNA (up to about 30–40 kb). In addition, use of the HSV latency-associated promoter allows high levels of expression of nucleic acids during periods of viral latency.

Viral vectors for in vivo expression of ECE nucleic acids can be administered to an individual via numerous routes, including orally, nasally, intravenously, intraperitoneally, intramuscularly, subcutaneously, intrathecally, intradermally, intracisternally or intraventricularly. Administration directly into the brain of an individual is one possible route to achieve expression of an ECE nucleic acid as provided for by the present invention. Alternatively, a viral vector can be administered, for example, intravenously, and targeted to the brain or engineered to cross the blood-brain barrier and be expressed in the brain.

Methods to target a virus to the brain for nucleic acid delivery or target expression of ECE sequences to the brain are known in the art. For example, the fiber knob of an adenovirus or the envelope protein of a retrovirus can be modified by attaching a ligand (e.g., an antibody or antibody fragment) that recognizes a brain-specific or neuron-specific receptor. In addition, methods of enhancing transport of molecules across the blood-brain barrier are known, and take advantage of passive diffusion (e.g, using electromagnetic fields, nitric oxide donors or sodium caprate) or receptor-mediated endocytosis (e.g., attachment of the virus particle to, for example, an anti-transferrin antibody or to putrescine). Expression of a viral vector carrying ECE nucleic acid sequence also can be targeted using brain-specific or neuron-specific promoter and/or transcriptional regulatory elements (see, for example, U.S. Pat. Nos. 5,976,872 or 6,066,726). A particularly useful promoter for neuronal-specific expression of an ECE nucleic acid is a prion promoter.

Administration of a genetically engineered virus to an individual and optimal expression of a nucleic acid encoding an ECE polypeptide is more effective with any or all of the following: a sufficient level of expression of the ECE nucleic acid; little or no expression of viral genes; minimal viral nucleic acid replication; no viral replication; minimal recombination between viruses (e.g., between genetically engineered viruses or between a genetically engineered virus and a non-genetically engineered virus); and minimal complementation of mutated or absent viral genes (e.g., a replication-deficient virus). In addition, it is desirable to avoid or eliminate any immune response in the individual (e.g., production of neutralizing antibodies) directed towards the virus.

In addition, an ECE polypeptide can be directly administered to an individual. ECE polypeptides can be administered to an individual via numerous routes, including nasally, intraventricularly, intravenously, intraperitoneally or intramuscularly. Administration directly into the brain of an individual is one possible route to increase ECE levels in the brain. Alternatively, the polypeptide can be administered, for example, intravenously, and targeted to the brain and/or engineered to cross the blood-brain barrier. Methods of targeting an ECE polypeptide to the brain are known in the art and are similar to those described above for targeting a virus to the brain of an individual.

Methods of monitoring the location and/or the amount of a viral vector or a polypeptide in an individual are known, and can include, for example, imaging a marker (e.g., a fluorophore) the product of a reporter gene (e.g., GFP) or a radioisotope (e.g., $^{99}$Tc) using methods known in the art, such as PET, nuclear, MR or optical imaging. In addition, levels of Aβ and/or ET can be measured in an individual to monitor the level of expression of an ECE polypeptide or expression of a viral-delivered ECE nucleic acid.

ECE and Hypertension

Since endothelins promote constriction, relaxation and proliferation of smooth muscle cells in the heart, kidney, endocrine glands and nervous system, inhibitors of ECE have received a large amount of pharmaceutical interest for their potential as anti-hypertension drugs. ECE inhibitors with different enzyme specificities and therapeutic potentials include, but are not limited to: compounds that also inhibit NEP, such as phosphoramidon, thiorphan, CGS 26303, CGS 26129; compounds based on the structure of phosphoramidon (e.g., (2,2 napthyl ethyl)PLT, S17162); analogues of big ET (e.g., [D-Val$^{22}$] big ET-1 (16–38), [Phe$^{22}$] big ET-1 (19–37)); inhibitors discovered from screening culture medium (e.g., Aspergillomarasmines, WS 79089B (FR 901533), WS 75624A+B); and several others (e.g., a hydroxamic acid derivative).

Given the results provided herein demonstrating that ECE inhibitors can block Aβ catabolism in cell culture and in vivo in guinea pigs, caution is warranted in using ECE-inhibitory drugs as a treatment of hypertension in humans. Inhibiting the activity of ECE for the purpose of treating hypertension may lead to the development of AD and/or acceleration of the disease in predisposed individuals. Further, because most ECE and NEP inhibitors can act on both enzymes, the use of these drugs in combination may be particularly risky.

The invention, therefore, features methods for identifying anti-hypertension compounds or candidate compounds that do not cause an increase in the level of Aβ. Numerous candidate compounds to treat hypertension already have been identified to date and methods to determine the effect of a particular compound on the catabolism of Aβ are described above. If necessary, the hypertensive effects of a compound can be evaluated using, for example, an animal model of hypertension. Spontaneously hypertensive rats (SHR) provide a model for hypertension studies. Mean arterial pressure (MAP), mean blood pressure (MBP), diastolic blood pressure (DBP) and heart rate (HR) can be monitored in SHRs (using, for example, a non-invasive tail cuff or catheterization of a femoral artery) prior to and following administration of a compound.

As used herein, "hypertension" typically refers to a condition of sustained elevated arterial BP, e.g., a sustained diastolic pressure in excess of 90 mm Hg in humans. Hypertension has been shown to result in significant cardiovascular damage throughout the body, e.g., congestive heart failure, coronary artery disease, stroke and/or progressive renal failure. Compounds having "anti-hypertension activity" refer to compounds that are able to reduce the level of hypertension in an individual or animal model.

A concern with administering compounds that up-regulate ECE for the therapeutic treatment of AD is that individuals may become hypertensive. Up-regulation of ECE activity in the periphery of mice injected with a construct to increase ECE expression, however, does not result in increased circulating endothelin levels, indicating that hydrolysis by ECE is not the rate-limiting step in the conversion of big-ET to ET. Further, even if increased ECE activity does augment endothelin levels, endothelin receptor antagonists can be administered in parallel to reduce or block any undesirable side effect of increased endothelin levels. In addition, ET receptors are an alternative and effective target for pharmacological interference of the endothelin system without affecting $A\beta$ catabolism.

The invention additionally features ECE-selective inhibitors (i.e., compounds that specifically or preferentially inhibit ECEs relative to other enzymes such as related zinc metalloendopeptidases) that are or have been modified such that the ECE-selective inhibitor does not effectively traverse the blood-brain barrier or the cell membrane. ECE-selective inhibitors that are cell-impermeable, and thus inhibit only ECE isoforms present on the cell-surface, can be therapeutically useful for treating hypertension. In addition, ECE-selective inhibitors that are blood-brain barrier-impermeable, and thus cannot inhibit catabolism of $A\beta$ in the brain, also can be therapeutically useful. Many classes of compounds that may potentially inhibit ECEs are already cell-impermeable or blood-brain barrier-impermeable (e.g., large chemical compounds or proteins), while compounds or classes of compounds that inhibit ECE and are cell- or blood-brain barrier-permeable can be modified such that transport across the cell membrane and/or blood-brain barrier is reduced or prevented. For example, the blood-brain barrier has a very low permeability to most hydrophilic molecules, and is typically impermeable to large proteins, such as corticosteroids or gonadotropin-releasing hormone. Therefore, a compound that inhibits ECE but can cross the blood-brain barrier can be modified by attaching a hydrophilic molecule or a large protein to the compound using methods known in the art (e.g., fusion proteins, or conjugation) to make such a compound blood-brain barrier-impermeable.

The invention will be further described in the following examples, which do not limit the scope of the invention described in the claims.

EXAMPLES

Example 1
Treatment of Guinea Pigs with Phosphoramidon

Animal experiments were conducted within the United States Department of Agriculture (USDA) and the National Institute of Health (NIH) guidelines for animal use and care. To prevent clotting and to facilitate the collection of plasma, each animal was given 100 USP units/kg heparin sodium salt (Sigma, St. Louis, Mo.) administered intraperitoneally (IP) prior to experimentation. Animals were anesthetized with a single IP injection of 0.9 mg/kg acepromazine maleate (Fermenta, Kansas City, Mo.) combined with 90 mg/kg Ketaset (Fort Dodge Laboratories, Fort Dodge, Iowa). Following complete anesthesia, the femoral vein on each leg was exposed and an indwelling, heparinized microcannula (BioTime, Inc., Berkeley, Calif.) was implanted into each femoral vein. During the entire operation, the animal's temperature was periodically monitored and anesthesia maintained by further intraperitoneal injections as necessary. Following successful catheterization, approximately 1 ml of blood was collected and the volume replaced with an equal volume of sterile saline (0.9% NaCl) supplemented with 100 USP units/ml heparin injected in the opposite catheter. Stock solutions of phosphoramidon (Boehringer, Indianapolis, Ind.) were diluted to the appropriate concentration in 1 ml saline and injected as a bolus. The time of drug administration was considered to be 0 hrs. At each respective time point, approximately 1 ml of blood was removed from the catheter opposite that used to inject the compound and an equal volume of saline solution containing 100 Units/ml heparin was reintroduced through the opposite catheter to maintain blood volume. Blood samples were immediately spun at 14,000×g for 5 min. Following centrifugation, plasma was transferred to a separate tube and frozen at −80° C. for subsequent analysis of $A\beta40$ and $A\beta42$ concentration by sandwich ELISA. Data was obtained from at least 2 animals, with the $A\beta$ in each sample measured at least twice.

Example 2

Measurement of $A\beta$

Human and guinea pig $A\beta40$ or $A\beta42$ was measured in plasma by sandwich ELISA as previously described (Suzuki et al., 1994, Science, 264:1336–1340) using the BAN-50/BA-27 or BAN-50/BC-05 antibody systems, respectively (Takeda; Japan). Hamster $A\beta40$- or $A\beta42$-derived from CHO cells was measured using the BNT-77/BA-27 or BNT-77/BC-05 antibody systems, respectively. $A\beta$ concentration in samples was determined by comparison to synthetic $A\beta40$ or $A\beta42$ standards (Bachem, Switzerland). Data was obtained from triplicate wells.

In particular, the sandwich ELISA used herein was performed as follows: 96-well microtiter plates were coated overnight at 4° C. with 100 $\mu$l of a 5 $\mu$g/ml dilution of primary antibody in sodium carbonate coating buffer (SCCB; 0.1 M $Na_2CO_3$, pH 9.6). Plates were blocked overnight at 4° C. with 300 $\mu$l of BLOCKAGE Solution (PBS+1.0% BLOCKAGE (Snow Brand Milk Products, Japan), 0.05% $NaN_3$, pH 7.4). Samples for analysis and synthetic $A\beta$ standards (Bachem, Switzerland) were diluted in buffer EC (0.02 M $NaH_2PO_4$, 0.002 M EDTA, 0.4 M NaCl, 0.2% BSA, 0.05% CHAPS, 0.04% BLOCKAGE, 0.05% $NaN_3$, pH 7.0) and allowed to incubate on the plates overnight at 4° C. Plates were washed twice with PBS (8 mM $Na_2HPO_4$, 1.5 mM $KH_2PO_4$, 139 mM NaCl, 2.7 mM KCl, pH 7.4) and 100 $\mu$l of secondary antibody directly coupled to HRP (EZ-LINK™ Plus Activated Peroxidase kit (contents of kit: peroxidase, 5 M sodium cyanoborohydride solution ($NaBH_3CN$), quenching buffer (3 M ethanolamine, pH 9.0), BupH™ phosphate buffered saline, BupH™ carbonate-bicarbonate buffer), according to manufacturers directions; Pierce Chemical Co., Rockford, Ill.) was allowed to bind either 4 hrs at room temperature or overnight at 4° C. Plates were then washed twice with PBS containing 0.05% Tween 20 followed by two additional washes in PBS. Detection was performed using TMB (3,3',5,5'-tetramethylbenzidine) as an HRP substrate according to the manufacturer's specifications (Kirkegaard & Perry Laboratories (KPL), Gaithersburg, Md.) and the reaction stopped by the addition of 100 μl of 1N H₃PO₄. Plates were read at 450 nm in a SpectraMax Plus spectrophotometer (Molecular Devices; Sunnyvale, Calif.) and analyzed by SOFTmax® PRO software. Aβ40 or Aβ42 were quantitated by comparison with the values obtained for each synthetic Aβ standard from the same plate.

Example 3
Cloning of Human ECE-1a and ECE-1b

For experiments described herein, ECE-1a and ECE-1b were each cloned by RT-PCR in two fragments (joined by a unique PvuII site) from human umbilical vein endothelial cells (HUVEC, ATCC Accession No. CRL-1730) using the primers shown in Table 1 (restriction sites are underlined).

TABLE 1

| PRIMER | SEQUENCE | SEQ ID |
|---|---|---|
| ECE-1a forward | 5'-CAGGAATTCGCCACCATGCCTCTCCAGGGCCTGGGCCTGC-3' | NO:1 |
| ECE-1b forward | 5'-CAGGAATTCGCCACCATGCGGGGCGTGTGGCCGCCC-3' | NO:2 |
| ECE-1 pvuII reverse | 5'-CAGCAGCTTCCCCAGCTGGACC-3' | NO:3 |
| ECE-1 PvuII forward | 5'-GGTCCAGCTGGGGAAGCTGCTG-3' | NO:4 |
| ECE-1 reverse | 5'-GCTCTAGATTACCAGACTTCGCACTTGTGAGGCGGG-3' | NO:5 |

RNA was prepared from HUVEC cells using the Qiagen RNeasy mini prep kit (Venlo, The Netherlands) and was reverse transcribed using Superscript II Reverse Transcriptase with an oligo-dT primer (Boehringer). The 5' fragment of ECE-1a was amplified using the ECE-1a forward and ECE-1 PvuII reverse primers. The 5' fragment of ECE-1b was amplified using the ECE-1b forward and the ECE-1 PvuII reverse primers. The 3' fragment of ECE-1, which is common to both isoforms, was amplified using the ECE-1 PvuII forward and the ECE-1 reverse primers. Pfu polymerase (Stratagene, La Jolla, Calif.) was used for all amplifications. The 5' and 3' fragments were ligated together at the PvuII site and subcloned into pCDNA3 (Invitrogen, Carlsbad, Calif.) using primer encoded EcoRI and XbaI sites. The sequences of the constructs were confirmed by dideoxy sequencing by the Mayo Molecular Biology Core Facility (Rochester, Minn.).

Example 4
Cell Culture and Transfections

Unless otherwise noted, cell culture reagents were purchased from Gibco BRL (Rockville, Md.) and cell lines were purchased from American Type Culture Collection (ATCC, 10801 University Blvd., Manassas, Va. 20110). HUVEC cells were cultured in Kaighn's F12K medium (ATCC) supplemented with 10% fetal bovine serum, 0.1 mg/ml heparin, 0.03 mg/ml endothelial cell growth supplement (Sigma), 100 units/ml penicillin and 100 μg/ml streptomycin. CHO cells were cultured in Ham's F12 medium (Bio Whittaker, Washington, D.C.) supplemented with 10% newborn calf serum, 100 units/ml penicillin and 100 μg/ml streptomycin. H4 cells (of human neuroglioma origin) were cultured in Opti-MEM medium (Gibco-BRL) supplemented with 10% fetal bovine serum, 100 units/ml penicillin and 100 μg/ml streptomycin. For passaging cells prior to experiments in which ECE activity was to be measured, a highly purified trypsin (Sigma, Catalog No. T-7418) solution was used. CHO cells were transfected with FuGENE 6 (Boehringer) according to the directions of the manufacturer. Stable lines were generated by selecting pCDNA3-transfected cells (ECE-1a or ECE-1b) with 1 mg/ml Geneticin or pSecTag-transfected cells (SolECE-1) with 0.8 mg/ml Zeocin (Invitrogen).

Example 5
Treatment of Cells with Metalloprotease Inhibitors

Cells were passaged into 6-well plates one day prior to treatment and grown to confluence. Triplicate wells were washed twice with Hank's balanced salt solution and then incubated for 17–24 hrs with 1 ml of growth medium containing phosphoramidon (34–100 μM), thiorphan (Sigma) or captopril (Sigma) at the appropriate concentrations. Control cells were incubated in growth medium containing an equal volume of vehicle (PBS). After treatment, the culture medium was harvested, spun at 14,000 xg, and the supernatant analyzed for Aβ40 or Aβ42 using sandwich ELISA and for secreted APP using Western blot. To assess cellular toxicity of the compounds, MTS assays (CELLTITER 96® (contents: tetrazolium compound [3-(4, 5-dimethylthiazol-2-yl)-5-(3-carboxymethoxyphenyl)-2-(4-sulfophenyl)-2H-tetrazolium, inner salt; MTS$^{(a)}$] and phenazine ethosulfate (PES)), Promega, Madison, Wis.), which measure the conversion of MTS to formazan by metabolically active cells, were performed on the cells after the indicated times. Culture medium was subjected to electrophoresis on 10–20% Tricine gels (Novex, Carlsbad, Calif.) and was subsequently transferred to Immobilon P (Millipore, Bedford, Mass.). Western blots on CHO cells were performed using a 22C11 antibody (Boehringer) to detect secreted APP. Bound antibody was detected by incubation with the appropriate HRP-linked secondary antibody (Amersham, Uppsala, Sweden) using ECL™ Western blotting reagents (Amersham) followed by exposure to X-ray film.

Example 6

Expression and Purification of Soluble ECE-1

A construct encoding a soluble form of ECE-1 was generated by amplifying the extracellular domain of ECE-1a using the primers shown in Table 2.

TABLE 2

| PRIMER | SEQUENCE | SEQ ID |
|---|---|---|
| SolECE-1 forward | 5'-GAGAGAATTCTCAGTACCAGACAAGATCCCC-3' | NO:6 |
| SolECE-1 reverse | 5'-CGTTTTCCTTTTGCGGCCGCCCAGACTTCGCACTTGTGAGG-3' | NO:7 |

The SolECE-1 construct was subcloned into pSecTag2B (Invitrogen) using primer-encoded EcoRI and NotI sites. This method incorporates a leader sequence into the N-terminus of the protein for secretion by mammalian cells, and sequential c-myc and 6×His tags at the C-terminus to facilitate detection and purification. The sequence of the construct was confirmed by dideoxy sequencing by the Mayo Molecular Biology Core Facility. A stable cell line that secretes soluble ECE-1 was generated by transfecting the SolECE-1 construct into CHO cells and selecting with Zeocin (0.8 mg/ml). At confluence, the cells were washed twice with Hank's balanced salt solution and cultured for 48 hrs in serum-free medium (CHO-S-SFM II). Conditioned medium was filtered through a 0.2 μm filter and dialyzed against binding buffer (0.05 M Na phosphate (pH 8.0), 0.3 M NaCl) prior to His-tag purification of the protein using Ni-NTA agarose (Qiagen). Bound protein was eluted from the Ni-NTA agarose with binding buffer containing 100 mM imidazole. The SolECE-1 was determined to be 25–50% pure by SDS-PAGE and Coomassie staining. To control for the presence of co-purifying native CHO proteins, conditioned serum-free medium from non-transfected CHO cells was purified as above, and the eluted proteins were used in control experiments.

Example 7
Aβ Degradation by SolECE-1

SolECE-1 (approximately 0.2 μM) was pre-incubated for 15 min at room temperature with the ECE inhibitors PD069185 (synthesized according to published methods (Ahn et al., 1998, *Biochem. Biophys. Res. Comm.*, 243:184–190) by the Mayo Clinic Organic Chemistry Core Facility, Jacksonville, Fla.) or phosphoramidon (150 μM), or an equal volume of vehicle (DMSO or PBS, respectively) prior to incubation with synthetic Aβ40 or Aβ42 (0.01 μM) in 50 mM MES (pH 6.5) containing 0.01% $C_{12}E_{10}$, 1 mM PMSF, 100 μM leupeptin, and 20 μM pepstatin. As a control, Aβ was incubated with Ni-NTA purified proteins from non-transfected CHO cells, or in reaction buffer alone. Following incubation for 24 hrs at 37° C., the reactions were stopped by the addition of 5 mM EDTA. Aβ concentration was then analyzed using a highly specific sandwich ELISA that captures Aβ via binding of antibody BAN-50 to the N-terminus, and detects only full-length Aβ peptides ending at residue 40 (using antibody BA-27) or 42 (using antibody BC-05). Thus, Aβ that has been further hydrolyzed will not be detected using this assay. To further analyze the degradation of Aβ by SolECE1, the enzyme was incubated with $^3$H labeled Aβ40 (0.56 μM, 2×10$^4$ dpm) as described above and resulting peptides were separated by reverse-phase chromatography.

Example 8
Treatment of Neuronal Cell Lines with Phosphoramidon

A dose-dependent, rapid increase in Aβ concentration was observed in the plasma of guinea pigs treated intravenously with phosphoramidon, indicating that phosphoramidon is capable of modulating Aβ accumulation in vivo. Treatment with metalloprotease inhibitors, in particular phosphoramidon, was previously shown to result in a rapid 2- to 3-fold increase in the concentration of Aβ40 and Aβ42 in the conditioned medium of neuronal cell lines. Likewise, a significant increase in extracellular Aβ concentration following treatment of H4 neuroblastoma cells with phosphoramidon also was reported.

To exclude the possibility that the phosphoramidon-induced effect was due to inhibition of extracellular degradation and/or internalization of Aβ by H4 cells, synthetic Aβ was spiked into the culture medium, incubated for 6 or 24 hrs, and the amount of synthetic Aβ remaining in the medium was determined by sandwich ELISA. Results showed that extracellular Aβ was removed equally in the presence or absence of phosphoramidon, indicating that the phosphoramidon-induced effect was not likely due to decreased internalization or to inhibition of a cell-surface or secreted protease. Results from a parallel set of culture wells in which synthetic Aβ was not added showed that phosphoramidon was promoting Aβ accumulation. Intracellular Aβ has not been convincingly detected in H4 cells, presumably due to rapid secretion of the peptide. The fact that removal of exogenous Aβ by H4 cells was insensitive to phosphoramidon clearly demonstrated that in H4 cells, the compound exerts its effect on Aβ through a predominantly intracellular event.

Example 9
Extracellular Concentration of Aβ Following Treatment of Cells with Phosphoramidon, Thiorphan or Captopril Phosphoramidon is known to inhibit several metalloproteases, including NEP, angiotensin converting enzyme (ACE) and ECE. Phosphoramidon does not inhibit insulin-degrading enzyme (IDE). Infusion of the metalloprotease inhibitor, thiorphan, into the brain of rats previously resulted in a significant increase in the amount of Aβ in the brain, and specifically, in the deposition of the longer, more amyloidogenic form of Aβ (i.e., Aβ42). This phenomenon in rats was attributed to the inhibition of extracellular Aβ degradation by NEP.

To identify the enzyme(s) responsible for the phosphoramidon-induced effect on Aβ concentration, H4 neuroglioma cells were treated with phosphoramidon or the NEP or ACE inhibitors, thiorphan or captopril, respectively. While phosphoramidon treatment resulted in a significant elevation in Aβ accumulation, treatment with thiorphan or captopril at concentrations greater than 1000-times the reported $IC_{50}$ for the respective target enzymes failed to result in increased extracellular Aβ, indicating that the phosphoramidon-induced effect in H4 cells was not due to inhibition of NEP or ACE. The presence of endogenous ECE activity in solubilized membranes of H4 cells was confirmed using a big-ET conversion assay. Mature endothelin was detected using a Biotrak Endothelin-1 Assay (Amersham Pharmacia, Catalog No. RPN228).

To further investigate whether inhibition of ECE might be responsible for the observed increase in Aβ concentration, the effect of phoshoramidon on CHO cells, which naturally lack ECE activity, was determined. Treatment with high concentrations of phosphoramidon did not affect the concentration of Aβ in the conditioned medium of CHO cells. Conversely, HUVEC cells, which naturally express high levels of endogenous ECE, had virtually undetectable levels of Aβ accumulation unless treated with high doses of phosphoramidon.

Example 10
Overexpression of ECE

To further investigate the role of ECE in Aβ accumulation, ECE-1b, which is localized almost exclusively intracellularly, and ECE-1a, which is localized predominantly to the plasma membrane but has also been detected within the cell, were cloned and the vectors used to transfect CHO cells. ECE activity, confirmed using a big ET-1 conversion assay, was present in solubilized membranes from the ECE-transfected cells and absent in vector-transfected cells. Overexpression of either ECE-1a or ECE-1b in these cells resulted in a striking 75–90% reduction in Aβ40 and a 45–60% reduction in Aβ42. No significant changes were observed in the amount of secreted APP accumulation in ECE-transfected cells compared to the vector controls, indicating that the cells were similarly viable and that secretion of ECE is not affected by ECE overexpression. The reduction in Aβ concentration in ECE-transfected cells was completely reversed by treatment with phosphoramidon, indicating that the observed reduction in Aβ was due to the enzymatic activity of the overexpressed ECE in transfected cells. As expected, since CHO cells lack endogenous ECE activity, Aβ concentration in the conditioned medium of non-transfected cells was unaffected by phosphoramidon treatment.

Extracellular Aβ removal in an endogenous ECE-expressing cell line, H4, was not affected by phosphoramidon treatment, indicating that the increase in Aβ concentration was likely due to an intracellular inhibition event. To determine whether extracellular removal of Aβ accounted, at least in part, for the dramatic decrease in extracellular Aβ concentration in ECE-transfected cell lines, synthetic Aβ40 was spiked into the culture medium in the presence or absence of phosphoramidon and the amount of unhydrolyzed Aβ was determined at 6 or 24 hrs by sandwich ELISA. After a 6 hr incubation, removal of Aβ was similar in the culture medium of ECE-transfected and untransfected CHO cells. Extracellular concentration of synthetic Aβ was not affected by phosphoramidon treatment, although secretion of endogenous Aβ in phoshoramidon-treated ECE-transfected cells was increased 1.5- to 2-fold during the same time period.

Following a 24 hr incubation, a significant increase in the removal of spiked Aβ in the medium of ECE-1a-transfected cells was observed compared to the non-transfected controls. No significant change in the removal of exogenous Aβ was observed in cells expressing the intracellular form of ECE (i. e., ECE-1b). The ECE-1a-induced increase in Aβ removal was completely attenuated by phosphoramidon treatment, indicating that the catabolism of Aβ was likely due to enzymatic activity of ECE-1a. Importantly, the phosphoramidon-induced accumulation of endogenous Aβ in parallel cultures of ECE-1a-transfected cells without synthetic Aβ was greater than 600% over the same time interval. These results suggest that, while ECE may also contribute to extracellular Aβ removal, especially in cells expressing isoforms present on the cell-surface, the major site of ECE's effect on Aβ is likely intracellular.

Example 11
Soluble ECE-1 Degrades Aβ In Vitro

To examine whether ECE is capable of direct catabolism of Aβ, a recombinant soluble form of ECE was generated (SolECE-1). Incubation of synthetic Aβ40 and Aβ42 with the purified enzyme resulted in almost complete loss of the peptides as detected by sandwich ELISA. This reduction was completely blocked by incubation with either phosphoramidon or the highly selective ECE inhibitor, PD069185. To confirm that this loss was indeed due to Aβ catabolism and not to Aβ binding or some other phenomenon, the effect of solECE-1 on Aβ was analyzed by HPLC using radiolabeled Aβ. Incubation of $^3$H-Aβ40 with solECE-1 resulted in the loss of the full-length (i.e., unhydrolyzed) Aβ and the formation of at least 4 novel peaks detected by reverse-phase chromatography. The formation of these peaks was completely blocked by treatment with PD069185.

Example 12
Knockout Mice

As ECE-2 is highly expressed in brain and is localized exclusively intracellularly, it is possible that the ECE-2 isozyme may in fact contribute to Aβ catabolism in the brain. ECE-2 (-/-) knockout mice were produced according to the method of Yanagisawa et al. (2000, *J. Clin. Invest.*, 105:1373–82) and obtained from Dr. Yanagisawa (University of Texas Southwestern Medical Center, Howard Hughes Medical Institute). Brains from adult ECE-2 (-/-) mice and wild-type littermates were homogenized in 70% formic acid and the neutralized extracts were analyzed for Aβ40 concentration by sandwich ELISA using the BNT-77/BA-27 antibody system. Results determined that Aβ40 levels were significantly elevated in the ECE-2 knockout mice compared to their wild-type littermates.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that increases the activity of an endothelin converting enzyme (ECE) polypeptide, the method comprising:

contacting Aβ with an ECE polypeptide in the presence of said compound; and detecting the amount of unhydrolyzed Aβ, wherein a decrease in the amount of unhydrolyzed Aβ produced in the presence of said compound compared to the amount of unhydrolyzed Aβ produced in the absence of said compound is an indication that said compound increases the activity of an ECE polypeptide.

2. The method of claim 1, wherein said ECE and said Aβ are in a cell.

3. The method of claim 1, wherein said unhydrolyzed Aβ is detected using an immunoassay.

4. The method of claim 1, wherein said compound is selected from the group consisting of a nucleic acid, a polypeptide, a chemical compound, a bacterial extract, a fungal extract, and a plant extract.

5. The method of claim 2, wherein said cell is selected from the group consisting of H4 neuroglioma cells, CHO cells, and HUVEC cells.

6. A method of identifying a compound that has anti-hypertension activity but does not cause an increase in the level of Aβ, the method comprising:

contacting Aβ with an ECE in the presence of said compound;

detecting the amount of unhydrolyzed Aβ, wherein lack of an increase in the amount of unhydrolyzed Aβ produced in the presence of said compound compared to the amount of unhydrolyzed Aβ produced in the absence of said compound is an indication that said compound does not cause an increase in the level of said ECE; and determining the anti-hypertension activity of said compound.

7. The method of claim 6, wherein the anti-hypertension activity of said compound is determined in an animal.

8. The method of claim 7, wherein said animal is a spontaneously hypersensitive rat (SHR).

9. The method of claim 6, wherein said unhydrolyzed Aβ is detected using an immunoassay.

10. The method of claim 7, wherein said compound is selected from the group consisting of a nucleic acid, a polypeptide, a chemical compound, a bacterial extract, a fungal extract, and a plant extract.

11. The method of claim 7, wherein said unhydrolyzed Aβ is detected in said animal.

12. A method of determining that an anti-hypertension compound or candidate compound does not cause an increase in the level of Aβ, wherein said anti-hypertension compound or candidate compound is an ECE inhibitor, the method comprising:

contacting Aβ with an ECE in the presence of said anti-hypertension compound or candidate compound; and detecting the amount of unhydrolyzed Aβ, wherein the lack of an increase in the amount of unhydrolyzed Aβ produced in the presence of said compound compared to the amount of unhydrolyzed Aβ produced in the absence of said compound is an indication that said compound does not cause an increase in the level of said ECE.

13. The method of claim 12, wherein said unhydrolyzed Aβ is detected using an immunoassay.

14. The method of claim 12, wherein said unhydrolyzed Aβ is detected in an animal.

15. The method of claim 12, wherein said compound is selected from the group consisting of a nucleic acid, a polypeptide, a chemical compound, a bacterial extract, a fungal extract, and a plant extract.

16. The method of claim 14, wherein said animal is a SHR.

* * * * *